United States Patent [19]

Flora et al.

[11] Patent Number: 4,761,406
[45] Date of Patent: Aug. 2, 1988

[54] REGIMEN FOR TREATING OSTEOPOROSIS

[75] Inventors: Lawrence Flora, Fairfield; Benjamin F. Floyd, Cincinnati, both of Ohio

[73] Assignee: The Procter & Gamble Company, Cincinnati, Ohio

[21] Appl. No.: 741,976

[22] Filed: Jun. 6, 1985

[51] Int. Cl.$^4$ .................... A61K 31/66; A61K 31/675
[52] U.S. Cl. ......................................... 514/86; 514/89; 514/107
[58] Field of Search .............................. 514/86, 89, 107

[56] References Cited

U.S. PATENT DOCUMENTS

| | | | |
|---|---|---|---|
| 3,683,080 | 8/1972 | Francis | 424/204 |
| 4,054,598 | 10/1977 | Blum et al. | 260/502.5 |
| 4,230,700 | 10/1980 | Francis | 424/204 |
| 4,330,537 | 5/1982 | Francis | 424/204 |

FOREIGN PATENT DOCUMENTS 100718 2/1984 European Pat. Off. .

OTHER PUBLICATIONS

Chesnut, "Synthetic Salmon Calcitonin, Diphosphonates, and Anabolic Steroids in the Treatment of Postmenopausal Osteoporosis", Osteoporosis–Proceedings of the Copenhagen International Symposium on Osteoporosis, Jun. 3–8, 1984, (Christiansen et al., Editors), Aalborg Stiftsbogtrykkeri (1984), pp. 549–555, see pp. 551–552.
Adami et al., "Dichloromethylene-Disphosphonate Therapy of Osteolytic Lesions and Osteoporosis", Osteoporosis–Proceedings of the Copenhagen International Symposium on Osteoporosis, Jun. 3–8, 1984, (Christiansen et al., Editors), Aalborg Stiftsbogtrykkeri (1984), pp. 643–645.
Reeve et al., "Studies of a 'Short-Cycle' ADFR Regime Using Parathyroid Peptide hPTH 1-34 in Idiopathic Osteoporosis and in a Dog Model," Osteoporosis–Proceedings of the Copenhagen International Symposium on Osteoporosis, Jun. 3–8, 1984, (Christiansen et al., Editors), Aalborg Stiftsbogtrykkeri (1984), pp. 567–573.
Rasmussen et al., "Effect of Combined Therapy with Phosphate and Calcitonin on Bone Volume in Osteoporosis," *Metab. Bone Dis. & Rel. Res.*, vol. 2, (1980), pp. 107–111.
Rasmussen, "Considerations as to the Pathogenesis and Treatment of Osteoporosis" in *Bone Histomorphometry 1980*, (Jee and Parifitt Editors), Armour-Montagu, Levallois, (1981), pp. 311–316.
Marie et al., "Treatment of Postmenopausal Osteoporosis with Phosphate and Intermittent Calcitonin", Osteoporosis–Proceedings of the Copenhagen International Symposium on Osteoporosis, Jun. 3–8, 1984, (Christiansen et al., Editors), Aalborg Stiftsbogtrykkeri, (1984), pp. 575–579.
Berthel et al., "Treatment of Post Menopausal Osteoporosis with Phosphate and Intermittent Calcitonin: Effect on Cortical Bone", Osteoporosis–Proceedings of the Copenhagen International Symposium on Osteoporosis, Jun. 3–8, 1984, (Christiansen et al., Editors), Aalborg Stiftsbogtrykkeri, (1984), pp. 651–652.
Ortolani et al., "Treatment of Postmenopausal and Senile Osteoporosis with Combined Calcitonin and 1.25-Dihydroxycholecalciterol", Osteoporosis–Proceedings of the Copenhagen International Symposium on Osteoporosis, Jun. 3–8, 1984, (Christiansen et al., Editors), Aalborg Stiftsbogtrykkeri, (1984), pp. 625–628.
Geusen and Dequeker, "Effect of Anabolic Steriods, 1-alpha Hydroxyvitamin D and Intermittent Calcium Infusions on Bone Mineral Content in Osteoporosis," pp. 665–667, Osteoporosis–Proceedings of the Copenhagen International Symposium on Osteoporosis, Jun. 3–8, 1984, (Christiansen et al., Editors), Aalborg Stiftsbogtrykkeri, (1984).
Delmas et al., "Cyclic Fluoride Therapy for Postmenopausal Osteoporosis", Osteoporosis–Proceedings of the Copenhagen International Symposium on Osteoporosis, Jun. 3–8, 1984, (Christiansen et al., Editors), Aalborg Stiftsbogtrykkeri, (1984), pp. 581–586.
Meunier et al., "Treatment of Primary Osteoporosis with Drugs that Increase Bone Formation: Sodium Fluoride, hPTH 1-34, ADFR Concept," Osteoporosis–Proceedings of the Copenhagen International Symposium on Osteoporosis, Jun. 3–8, 1984, (Christiansen et al., Editors), Aalborg Stiftsbogtrykkeri, (1984), pp. 595–602.
Kleerekoper et al., "Treatment of Osteoporosis with Sodium Fluoride Alternating with Calcium and Vitamin D", Osteoporosis: Recent Advances in Pathogenesis and Treatment, (DeLuca et al., Editors), University Park Press, Baltimore, MD, (1981), pp. 441–448.
Briancon and Meunier, "Treatment of Osteoporosis with Fluoride, Calcium, and Vitamin D", *Orthop. Clin. N. Amer.*, vol. 12, (1981), pp. 629–648.
Siris et al., "Long-Term Therapy of Paget's Disease of Bone with EHDP", *Arthritis and Rheumatism*, 23(10), pp. 1177–1184, (1980).
Meunier et al., "Effects of Disodium Dichloromethylene Diphosphonate on Paget's Disease of Bone," *Adv. Exp. Med. Biol.*, 128, pp. 299–309, (1980).
Anderson et al., "Preliminary Observations of a Form of Coherence Therapy for Osteoporosis", *Calcif. Tissue Int.*, vol. 36, (1984), pp. 341–343.
Frost, "*Editorial*—the ADFR Concept Revisited", *Calcif. Tissue Int.*, vol. 36, (1984), pp. 349–353.

(List continued on next page.)

Primary Examiner—Stanley J. Friedman
Attorney, Agent, or Firm—Milton B. Graff, IV; Steven J. Goldstein; Jack D. Schaeffer

[57] ABSTRACT

A method for treating or preventing osteoporosis utilizing a cyclic regimen comprising alternating for two or more cycles the administration of a bone resorption inhibiting polyphosphonate and a no treatment (rest) period. Further disclosed is a kit for use in implementing this method of treatment.

21 Claims, No Drawings

OTHER PUBLICATIONS

Recker, "Stimulation of New Bone Formation by the 'ADFR' Technique in Dogs", in *Bone Histomorphometry 1980*, (Jee and Parifitt Editors), Armour-Montagu, Levallois, (1981), pp. 331-336.

Bonjour et al., "Action of 1,25-Dihydroxyvitamin $D_3$ and a Diphosphonate in Calcium Metabolism in Rats", *Amer. J. Physiology*, vol. 229, (1975), pp. 402-408.

Bonjour et al., "Influence of 1,25-Dihydroxycholecalciferol and Diphosphonate on Calcium Metabolism", *Experientia*, vol. 29, (1973), p. 740.

Boris et al., "Evidence for the Promotion of Bone Mineralization by 1-alpha, 25-Dihydroxycholecalciferol in the Rat Unrelated to the Correction of Deficiencies in Serum Calcium and Phosphorus", *J. Nutr.*, vol. 108 (1978), pp. 1899-1906.

Boris, et al., "Effect of Diphosphonates on Bone Mineralization and Serum Levels of 1-alpha, 25-Dihydroxyvitamin D in Rats," *Proceedings of the Workshop on Vitamin D*, 1982, pp. 809-811, (1982).

Boris, et al., "Effect of Diphosphonates on Bone Mineralization and Serum Levels of 1-alpha. 25-Dihydroxyvitamin D in Rats", Abstract from the Fifth Workshop on Vitamin D, Historic Williamsburg, Virginia, Feb. 14-19, 1982.

Frost, "Treatment of Osteoporosis by Manipulation of Coherent Bone Cell Populations *Clin. Orth. Rel. Res.*, vol. 143, (1979), pp. 227-244.

Frost, "The ADFR Concept and Monitoring It", in *Bone Histomorphometry 1980*, (Jee and Parifitt Editors), Armour-Montagu, Levallois, (1981), pp. 317-321.

Frost, "The Evolution of Osteoporosis Therapy", *Orthop. Clin. N. Amer.*, vol. 12, (1981), pp. 603-610.

Frost, "Coherence Treatment of Osteoporoses", *Orthop. Clin. N. Amer.*, vol. 12, (1981), pp. 649-669.

Frost, "Clinical Management of the Symptomatic Osteoporotic Patient", *Orthop. Clin. N. Amer.*, vol. 12, (1981), pp. 671-681.

Frost, "Osteoporoses: Quo Vadis", *Orthop. Clin. N. Amer.*, vol. 12, (1981), pp. 683-691.

Frost, "*Review Article*—The Skeletal Intermediary Organization", *Metab. Bone Dis. & Rel. Res.*, vol. 4, (1983), pp. 281-290.

Francis and Martodam, "CH. 4-Chemical, Biochemical, and Medicinal Properties of the Diphosphonates," in *The Role of Phosphonates in Living Systems*, (Hildebrand, Editor), CRC Press, Inc., Boca Raton, Fla., (1983), pp. 55-96.

Recker, "Continuous Treatment of Osteoporosis: Current Status", *Orthop. Clin. N. Amer.*, vol. 12, (1981), pp. 611-627.

REGIMEN FOR TREATING OSTEOPOROSIS

TECHNICAL FIELD

The present invention relates to a method of treating or preventing osteoporosis. Specifically, the present invention relates to a well-defined regimen for the intermittent dosing, in a limited amount for a limited time, of certain polyphosphonate compounds. The present invention further relates to a kit to be used by patients for effectively implementing the method of treatment of the present invention.

BACKGROUND OF THE INVENTION

Osteoporosis is the most common form of metabolic bone disease. Although it may occur secondary to a number of underlying diseases, 90% of all cases appear to be idiopathic. Postmenopausal women are particularly at risk to idiopathic osteoporosis ("postmenopausal osteoporosis"). Another high risk group for idiopathic osteoporosis are the elderly of either sex ("senile osteoporosis").

In the various forms of osteoporosis, bone fractures, which are the result of bone loss that has reached the point of mechanical failure, frequently occur. Postmenopausal osteoporosis is characterized by fractures of the wrist and spine. Femoral fractures seem to be the dominant feature of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, the rate at which osteoclasts and osteoblasts are formed is such that bone formation and bone resorption are in balance. However, in osteoporotics an imbalance in the bone remodeling process develops which results in bone being lost at a rate faster than it is being made. Although this imbalance occurs to some extent in most individuals as they age, it is much more severe and occurs at a younger age in osteoporotics.

There have been many attempts to treat osteoporosis with a variety of pharmacologic agents with the goal being to either slow further bone loss or, more desirably, to produce a net gain in bone mass. It appears as though there are agents available, such as estrogen, which will slow further bone loss in osteoporotics, but agents or methods of treatment which will result in the replacement of bone which has already been lost have been very elusive.

The ability of polyphosphonates to inhibit bone loss has been well documented in animals and man. However, these compounds have, thus far, not proven to be particularly useful in diseases such as osteoporosis where there is chronic loss of bone, and therefore a perceived need for chronic treatment. The reason for this probably lies in the tight coupling between the bone resorption and formation in the human skeleton. When one attempts to chronically manipulate one phase of the skeletal remodeling cycle (bone resorption or formation), a similar effect occurs in the opposing process and any change produced in then negated. In the case of polyphosphonates, chronic inhibition of bone resorption tends to produce chronic inhibition of bone formation. Furthermore, long term chronic inhibition of remodeling is not desirable since it appears that this may lead to the development of spontaneous bone fractures.

It has now been discovered that bone loss can be inhibited and bone mass can be increased if certain polyphosphonates are given, in a limited amount, according to a specific regimen of intermittent, rather than chronic, dosing. This regimen forms the heart of the present invention. This treatment apparently uncouples bone resorption and formation by selectively inhibiting the resorption phase of bone remodeling without appreciably affecting the formation phase, and thus producing the net increase in skeletal mass.

It is therefore an object of the present invention to provide a method for treating or preventing osteoporosis which does not require prolonged administration of pharmacologic agents, and which does not result in a significant inhibition of bone formation.

A further object of the present invention is to provide a kit to facilitate the necessary strict compliance with the method of treatment of the present invention.

U.S. Pat. No. 3,683,080, to Francis (issued Aug. 8, 1972), discloses pharmaceutical compositions containing polyphosphonate compounds. These compositions are useful for inhibiting deposition and mobilization of calcium phosphates in animal tissue. This patent also discloses a method for treating or preventing conditions involving pathological calcification and hard tissue demineralization, such as osteoporosis, in animals by utilizing the chronic dosing of these compositions.

U.S. Pat. No. 4,230,700, to Francis (issued Oct. 28, 1980), discloses the conjoint administration of certain polyphosphonate compounds, in particular diphosphonates, and vitamin D-like anti-rachitic compounds for inhibition of the anomalous mobilization of calcium phosphate in animal tissue. See also U.S. Pat. No. 4,330,537, to Francis (issued May 18, 1982). The patents specify that the administration of the phosphonate and the vitamin D-like compounds be conjoint.

Siris et al., *Arthritis and Rheumatism*, 23 (10), 1177–1184 (1980), discloses research into intermittent therapy for Paget's disease involving high doses of EHDP or long periods of treatment with EHDP.

Rasmussen et al., "Effect of Combined Therapy with Phosphonate and Calcitonin on Bone Volume in Osteoporosis", *Metabolic Bone Disease and Related Research*, 2, 107, (1980), discloses a treatment regimen consisting of continuous administration of inorganic phosphate and intermittent administration of calcitonin.

Anderson et al., *Calcified Tissue International*, 36, 341–343 (1984), discloses a sequential and intermittent method of treating osteoporosis based on the ADFR theory of bone treatment which requires a period during which a bone activation compound, such as inorganic phosphate, is administered to the patient, to be followed by a period during which a bone resorption repressing compound, such as ethane-1-hydroxy-1,1-diphosphonic acid, is administered, followed by a period free of medication to allow the bone to be built up.

SUMMARY OF THE INVENTION

The present invention relates to a method of treating or preventing osteoporosis, in humans or lower animals afflicted with or at risk to osteoporosis, utilizing a regimen comprising two or more cycles, whereby each cycle comprises a period of from about 1 day to about 90 days during which a bone resorption inhibiting polyphosphonate is administered daily in a limited and effective amount, and a rest period of from about 50 days to about 120 days during which no bone resorption inhibiting agent is administered.

The present invention further relates to a kit for use in the above-described cyclic regimen, said kit containing the following components: from about 1 to about 90 daily doses, with each daily dose containing a limited and effective amount of a bone resorption inhibiting polyphosphonate; from about 50 to about 120 daily doses of a placebo or a nutrient supplement; and a means for having the components arranged in a way as to facilitate compliance with the regimen.

DETAILED DESCRIPTION OF THE INVENTION

The present invention relates to a method of treating or preventing osteoporosis, in humans or lower animals afflicted or at risk to osteoporosis, utilizing a cyclic regimen consisting of two or more cycles, whereby each cycle comprises: (a) a period of from about 1 day to about 90 days during which a bone resorption inhibiting polyphosphonate is administered daily in a limited and effective amount, preferred amount being from about 0.25×LED to about 4×LED, with from about 0.25×LED to about 2.5×LED most preferred; and (b) a rest period of from about 50 days to about 120 days, preferred being from about 70 days to about 100 days, with about 84 days most preferred. This regimen is particularly effective in preventing bone loss, and causing bone mass to increase, in subjects afflicted with or at risk to osteoporosis.

Each cycle within the regimen may be of equal length or the cycles may vary in length. Either the length of time during which the bone resorption polyphosphonate is administered, and/or the length of the rest period may be varied from cycle to cycle. In addition, the bone resorption inhibiting polyphosphonate may be the same or different from cycle to cycle (e.g., alternating cycles using ethane-1-hydroxy-1,1-diphosphonate one cycle and dichloromethane diphosphonate the next cycle), with preferred being the same bone resorption inhibiting polyphosphonate being used each cycle.

Examples of the cycle times within a regimen are:

(1) 14 days of daily treatment with a bone resorption inhibiting polyphosphonate, alternating with an 84 day rest period;

(2) 42 days of daily treatment with a bone resorption inhibiting polyphosphonate, alternating with a 56 day rest period;

(3) 56 days of daily treatment with a bone resorption inhibiting polyphosphonate, alternating with a 112 day rest period;

(4) 28 days of daily treatment with a bone resorption inhibiting polyphosphonate, followed by an 84 day rest period, followed by 84 days of daily treatment with a bone resorption inhibiting polyphosphonate, followed by an 84 day rest period, followed by 28 days of daily treatment, followed by an 84 day rest period.

Preferred cycle times of the present invention are given in (1), above, with the preferred bone resorption inhibiting polyphosphonate for this example being ethane-1-hydroxy-1,1-diphosphonic acid, and its pharmaceutically-acceptable salts and esters. Also preferred is the cycle times in (4), above, with dichloromethane diphosphonic acid, and its pharmaceutically-acceptable salts and esters, preferred as the bone resorption inhibiting polyphosphonate for this particular regimen.

The total treatment time (i.e., the number of cycles for treatment) for the method of treatment of the present invention will vary from patient to patient based on sound medical judgment and factors particular to the patient being treated such as, for example, the extent of bone loss prior to starting treatment, the age and physical condition of the patient, and whether the goal of the treatment is to prevent bone loss or build bone mass. For example, if a certain percent increase in bone mass is desired from the method of treatment of the present invention, the total treatment time is as long as it takes to obtain this goal as determined through bone measurement. Those skilled in the art known the factors to be considered, and can easily determine the total treatment time based on these factors on a patient by patient basis.

By "human or lower animal afflicted with or at risk to osteoporosis" as used herein is meant a subject diagnosed as suffering from one or more of the various forms of osteoporosis, or a subject belonging to a group known to have a significantly higher than average chance of developing osteoporosis, e.g., postmenopausal women, men over age 65, and persons being treated with drugs known to cause osteoporosis as a side effect (such as adrenocorticoids).

By "bone resorption inhibiting polyphosphonate" as used herein is meant polyphosphonate compounds and compositions of the type disclosed in U.S. Pat. No. 3,683,080, to Francis (issued Aug. 8, 1972); U.S. Pat. No. 4,054,598, to Blum and Worms (issued Oct. 18, 1977); U.S. Pat. No. 4,330,537, to Francis (issued May 18, 1982); U.S. patent application Ser. No. 684,544, Benedict and Johnson (filed Dec. 21, 1984); U.S. patent application Ser. No. 684,543, Benedict and Perkins (filed Dec. 21, 1984); European Patent Application No. 100,718, Breliere et al. (published Feb. 15, 1984); the disclosures of all of which are incorporated herein by reference. The term "phosphonate" includes the phosphonic acids, as well as their pharmaceutically-acceptable salts and esters. Preferable polyphosphonates are geminal diphosphonates (also referred to as bis-phosphonates or diphosphonates).

Bone resorption inhibiting polyphosphonates useful for the method of treatment of the present invention include, but are not limited to, those having the general formula:

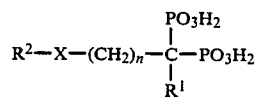

wherein n is an integer from 0 to about 7, with preferred n being 0, 1, or 2; $R^1$ is hydrogen, chloro, amino, or hydroxy, with $R^1$ being hydrogen or hydroxy preferred; X is —NH—, oxygen, or a single bond, with X being —NH— or single bond preferred; $R^2$ is a nitrogen-containing six-membered aromatic ring, or hydrogen; and their pharmaceutically-acceptable salts and esters.

Specific examples of bone resorption inhibiting polyphosphonates include:
ethane-1-hydroxy-1,1-diphosphonic acid,
pentane-1-hydroxy-1,1-diphosphonic acid, methane diphosphonic acid,
methane-dichloro-diphosphonic acid,
methane-hydroxy-diphosphonic acid,
ethane-1-amino-1,1-diphosphonic acid,
ethane-2-amino-1,1-diphosphonic acid,
propane-3-amino-1,1-diphosphonic acid,
propane-3-amino-1-hydroxy-1,1-diphosphonic acid,
propane-N,N-dimethyl-3-amino-1-hydroxy-1,1-diphosphonic acid,
propane-3,3-dimethyl-3-amino-1-hydroxy-1,1-diphosphonic acid,
phenyl-amino-methane-diphosphonic acid,
N,N-dimethyl-amino-methane-diphosphonic acid,
N-(2-hydroxyethyl)-amino-methane-diphosphonic acid,
butane-4-amino-1-hydroxy-1,1-diphosphonic acid,
pentane-5-amino-1-hydroxy-1,1-diphosphonic acid,
hexane-6-amino-1-hydroxy-1,1-diphosphonic acid,
indan-2,2-diphosphonic acid;
hexahydroindan-2,2-diphosphonic acid;
2-methylcyclobutane-1,1-diphosphonic acid;
3-chlorocyclopentane-1,1-diphosphonic acid;
cyclohexane-1,1-diphosphonic acid;
2-(2-pyridyl)-1-hydroxy-ethane-1,1-diphosphonic acid;
N-(2-(5-amino)-pyridyl)-aminomethane diphosphonic acid;
N-(2-(5-chloro)-pyridyl)-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-pyrimidyl)-aminomethane diphosphonic acid;
N-(2-pyridyl)-2-aminoethane-1,1-diphosphonic acid;
2-(2-pyridyl)-ethane-1,1-diphosphonic acid;
2-(3-pyridyl)-ethane-1,1-diphosphonic acid;
2-(4-pyridyl)-ethane-1,1-diphosphonic acid;
2-(2-(3-picolyl))-oxaethane-1,1-diphosphonic acid; and
pharmaceutically-acceptable salts and esters thereof.

Preferred bone resorption inhibiting polyphosphonates for use in the regimen of the present invention are:
ethane-1-hydroxy-1,1-diphosphonic acid ("EHDP");
dichloromethane diphosphonic acid ("Cl$_2$MDP");
propane-3-amino-1-hydroxy-1,1-diphosphonic acid ("APD");
hexane-6-amino-1-hydroxy-1,1-diphosphonic acid ("AHDP");
butane-4-amino-1-hydroxy-1,1-diphosphonic acid ("ABDP");
2-(2-pyridyl)-ethane-1,1-diphosphonic acid ("pyr-EDP");
2-(2-pyridyl)-1-hydroxy-ethane-1,1-diphosphonic acid ("pyr-EHDP");
hexahydroindan-2,2-diphosphonic acid ("HIP"); and
pharmaceutically-acceptable salts and esters thereof.

By "pharmaceutically-acceptable salts and esters" as used herein is meant hydrolyzable esters and salts of the diphosphonate compounds which have the same general pharmacological properties as the acid form from which they are derived, and which are acceptable from a toxicity viewpoint. Pharmaceutically-acceptable salts include alkali metal (sodium and potassium), alkaline earth metal (calcium and magnesium), non-toxic heavy metal (stannous and indium), and ammonium and low molecular weight substituted ammonium (mono-, di- and triethanolamine) salts.

An important aspect of the present invention is the discovery that too high a dosage of bone resorption inhibiting polyphosphonate is detrimental to bone formation when following the intermittent dosing regimen according to the present invention. For this reason, the method of treatment of the present invention requires that the daily dosages of the bone resorption inhibiting polyphosphonates be given in a specific limited and effective amount. The limited and effective amount of polyphosphonate to be used in the present invention is a daily dosage for the bone resorption inhibiting polyphosphonate which is based on the potency of the polyphosphonate as a bone resorption inhibiting agent (as determined by the thyroparathyroidectomized ("TPTX") rat model) in light of the characterization of the polyphosphonate as being EHDP-like or Cl$_2$MDP-like (this characterization being based on the tendency of the polyphosphonate to inhibit bone mineralization relative to bone resorption inhibition as determined by the Schenk model).

The limited and effective amount of polyphosphonate which is to be administered daily according to the method of treatment of the present invention is therefore determined by a two step process. First, the polyphosphonate must be characterized as being EHDP-like or Cl$_2$MDP-like based on the polyphosphonate's tendency to inhibit bone mineralization relative to its ability to inhibit bone resorption. This relative tendency to inhibit bone mineralization is determined by the Schenk model described hereinbelow, and is measured by the difference between the lowest effective dose ("LED") of the polyphosphonate to inhibit bone resorption (as determined by the Schenk model) and the lowest dosage producing widening of epiphyseal growth plate (which is a measure of mineralization inhibition). Polyphosphonates that have a difference between these two values of about one log dose or less (i.e., the dose at which mineralization inhibition is observed is less than or equal to about 10 times the LED for bone resorption inhibition) are characterized as being EHDP-like, i.e., they have a strong relative tendency to inhibit bone mineralization. Polyphosphonates that have a difference between these two values greater than about one log dose (i.e., the dose at which mineralization inhibition is observed is greater than about 10 times the LED for bone resorption inhibition) are characterized as being Cl$_2$MDP-like, i.e., they have little relative tendency to inhibit bone mineralization.

Bone resorption inhibition LEDs and mineralization inhibition dose values for representative polyphosphonates, determined by the Schenk model, are given in Tables II and III below. Non-limiting examples of EHDP-like polyphosphonates are: EHDP and N-(2-pyridyl)-aminomethane diphosphonic acid ("N-(2-pyr)AMDP"). Non-limiting examples of Cl$_2$MDP-like polyphosphonates are; Cl$_2$MDP, APD, AHDP, ABDP and pyr-EDP.

The second step (for deciding the limited and effective amount of polyphosphonate to be administered daily) is determining the daily oral dosages for the bone resorption inhibiting polyphosphonates based on the potency of the polyphosphonate as a bone resorption inhibiting agent. This potency is determined by means of the thyroparathyroidectomized (TPTX) rat model described herein and expressed as the lowest effective dose (LED) of the compound which is defined as the lowest subcutaneously given dose of polyphosphonate, in mg P per kg body weight, which in the TPTX rat model results in an inhibition of the PTH-induced rise in serum calcium level. Since the amount of polyphosphonate to be administered is dependent on the bone resorption inhibition potency of the compound, the amount to be administered is conveniently expressed as multiples of LED. Extrapolation of the dosages for polyphosphonates from the TPTX rat model to humans is possible based on the observation that oral dosages in humans are proportionally related to the LEDs for polyphosphonates in the TPTX rat model.

It is necessary for the method of treatment of the present invention that the daily oral dosage for EHDP-like polyphosphonates be in the range of from about $0.25 \times$ LED to about $4 \times X$ LED, with from about $0.25 \times$ LED to about $2.5 \times$ LED preferred. The range for $Cl_2MDP$-like polyphosphonates is from about $0.25 \times$ LED to about $10 \times$ LED, with preferred being from about $0.25 \times$ LED to about $4 \times$ LED, and from about $0.25 \times$ LED to about 2.5 LED most preferred. Thus, by "limited and effective amount" as used herein is meant daily oral dosages for EHDP-like polyphosphonates that fall within the range of from about $0.25 \times$ LED to about $4 \times$ LED, and daily oral dosages for $Cl_2MDP$-like polyphosphonates that fall within the range of from about $0.25 \times$ LED to about $10 \times$ LED. In particular, preferred is a daily oral dosage of about $1.25 \times$ LED of DIDRONEL (Norwich Eaton Pharmaceuticals, Norwich, NY; disodium EHDP in a dose of about 5 mg/kg/day). Further particularly preferred is a daily oral dosage of about $8 \times$ LED of $Cl_2MDP$, or its pharmaceutically-acceptable salt or ester (about 20 mg/kg of the disodium salt of $Cl_2MDP$). It is these critical dosage limitations, in combination with the cycle times of the method of treatment of the present invention, that distinguishes the present invention from other regimens of the art which utilized higher dosages and/or longer cycle times (e.g., Sirls et al., Arthritis and Rheumatism, 23 (10), 1177-1184 (1980)). The LEDs for a number of polyphosphonates are collected in Table I.

Ranges for the daily administration of some polyphosphonates for subjects afflicted with or at risk to osteoporisis are therefore: EHDP: from about 0.25 mg P/kg to about 4 mg P/kg, with from about 0.25 mg P/kg to about 2.5 mg P/kg preferred; $Cl_2MDP$: from about 0.12 mg P/kg to about 5 mg P/kg, with from about 0.12 mg P/kg to about 2 mg P/kg preferred, and from about 0.12 mg P/kg to about 1.25 mg P/kg most preferred; APD: from about 0.025 mg P/kg to about 1 mg P/kg, with from about 0.025 mg P/kg to about 0.4 mg P/kg preferred, and from about 0.025 mg P/kg to about 0.25 mg P/kg most preferred; ABDP: from about 0.0025 mg P/kg to about 0.1 mg P/kg, with from about 0.0025 mg P/kg to about 0.04 mg P/kg preferred, and from about 0.0025 mg P/kg to about 0.025 mg P/kg most preferred; AHDP: from about 0.025 mg P/kg to about 1 mg P/kg, with from about 0.025 mg P/kg to about 0.4 mg P/kg preferred, and from about 0.025 mg P/kg to about 0.25 mg P/kg most preferred; pyr-EDP: from about 0.0025 mg P/kg to about 0.1 mg P/kg, with from about 0.0025 mg P/kg to about 0.04 mg P/kg preferred, and from about 0.0025 mg P/kg to about 0.025 mg P/kg most preferred; pyr-EHDP: from about 0.00025 mg P/kg to about 0.01 mg P/kg, with from about 0.00025 mg P/kg to about 0.004 mg P/kg preferred, and from about 0.00025 mg P/kg to about 0.0025 mg P/kg most preferred; and HIP: from about 0.25 mg P/kg to about 10 mg P/kg, with from about 0.25 mg P/kg to about 4 mg P/kg preferred, and from about 0.25 mg P/kg to about 2.5 mg P/kg most preferred.

The preferred mode of administration for the polyphosphonates used in the present invention is orally, but other modes of administration may be used including, without limitation, intramuscular, intravenous, intraperitoneal, and subcutaneous administration, as well as topical application. Adjustment of oral dosage levels to doses to be administered other than orally is disclosed in the above cited patents and applications which have been incorporated herein by reference. Adjustment of the above preferred oral doses for dosing other than orally can easily be made by those skilled in the art. The daily administration of the bone resorption inhibiting polyphosphonates may consist of one dose every 24 hours, or several doses within the 24-hour period. Up to about 4 single dosages per day may be administered.

The length of time during which the bone resorption inhibiting polyphosphonate is administered is from about 1 day to about 90 days. It is preferred that EHDP-like polyphosphonates be administered from about 1 to about 30 days, with about 7 to about 21 days most preferred. It is further preferred that $Cl_2MDP$-like polyphosphonates be administered from about 30 to about 90 days, with about 80 to about 90 days preferred. It is particularly preferred that EHDP-like polyphosphonates, especially EHDP, be administered for 14 days, and followed by an 84 day rest period. Also particularly preferred is that $Cl_2MDP$-like polyphosphonates, especially $Cl_2MDP$, be administered for 84 days, and followed by an 84 day rest period.

When a relatively short period of time is used for dosing the bone resorption inhibiting polyphosphonate (e.g., a 1 day dosing period), a relatively high dose (within the above stated ranges) of the bone resorption inhibiting polyphosphonate is preferred. Also for a relatively short period of dosing the polyphosphonate, it is preferred that the method of administering the polyphosphonate be a more efficient method of administration than oral administration, e.g., intravenous or subcutaneous.

By "rest period" as used herein is meant a period of time during which the patient is not given a bone resorption inhibiting polyphosphonate, nor is the patient subjected to a bone cell activating amount of a bone cell activating compound or other conditions which would result in significant activation or inhibition of new bone remodeling units ("BRU"; the packet of bone turnover in the adult skeleton) during this time. It is this fact which further distinguishes the present invention from other regimes of the art (see, e.g., Rasmussen et al., "Effect of Combined Therapy with Phosphonate and Calcitonin on Bone Volume in Osteoporosis", *Metabolic Bone Disease and Related Research*, 2, 107, (1980) and Anderson et al., *Calcified Tissue International*, 36, 341-343 (1984)), which require the use of a bone cell activating compound all the time (e.g., Rassmussen et al.) or during part of the rest period (e.g., Anderson et al.).

By "bone cell activating compound" as used herein is meant a compound which increases the rate of activation of new BRU's. The concepts and terminology relating to bone cell activation are described in more detail in Frost, *Clinical Orthopedics and Related Research*, 143, 227-244 (1979); Rasmussen et al., *Metabolic Bone Disease and Related Research*, 2, 107-111 (1980); Frost, *Metabolic Bone Disease and Related Research*, 4, 281-290 (1983); and Frost, *Orthopedic Clinics of North America*, 12, 692-737 (1981); the disclosures of all of which are incorporated herein by reference. In most cases this increased rate of activation is initially manifested by an increase in the number of bone resorbing cells and bone resorbing sites. Biochemical indices of skeletal remodeling, such as urinary hydroxyproline levels, are expected to become elevated according to the magnitude of the response to the bone cell activating compound. Specific examples of such compounds are parathyroid hormone (PTH), inorganic phosphate, growth hormone, fluoride, thyroid hormones (e.g. thyroxine), certain vitamin D metabolites and prostaglandins.

By "bone cell activating amount" as used herein is meant an amount of the bone cell activating compound sufficient to effect a medically significant increase in the rate of activation of new BRUs. Specific examples of bone cell activating compounds, and their bone cell activating amounts, are: inorganic phosphate: above about 4 mg/kg/day (P.O.) of phosphorous; 1,25-dihydroxy vitamin $D_3$ and other 1-hydroxy vitamin D metabolites: above about 0.001 microgram/kg/day (P.O.); 25-hydroxy vitamin $D_3$ and other 25-hydroxy vitamin D metabolites (not including 1,25-dihydroxy vitamin D metabolites); above about 0.1 microgram/kg/day (P.O.); inorganic fluoride (e.g. sodium fluoride); above about 0.1 mg/kg/day F per day (P.O.); thyroxine: above about 0.01 mg/kg/day (P.O.); triiodothyroxine; above about 0.1 microgram/kg/day (P.O.); prostaglandin $PGE_2$: above about 0.1 mg/kg/day (P.O.); parathyroid hormone 1–34: above about 0.1 microgram/kg/day (S.C.).

However, this is not to say that no chemicals may be administered to the patient during the rest period. Nutrient supplements like calcium, vitamin D (to be distinguished from bone cell activating amounts of bone cell activating metabolites of vitamin D) iron, niacin, vitamin C and other vitamin or mineral supplements (which do not significantly affect the BRUs) can beneficially be administered during the rest period. Certain medications which do not significantly affect the BRUs, such as, for example, antibiotics (e.g., penicillin), may also be administered during the rest period. However, medications which significantly affect the BRUs, such as, e.g., calcitonin and adrenocorticosteroids, are not to be administered during the rest period. A placebo (e.g., a sugar pill) may also be administered during the rest period to assist in following the regimen of the present invention, especially if no daily supplement is being given during the rest period and for use in a kit of the present invention.

While a rest period as short as about 30 days may be utilized, it is preferred for the present invention that the rest period, for all polyphosphonates, be from about 50 days to about 120 days. More preferred, for all polyphosphonates, is a rest period of from about 70 days to about 100 days, with about 84 days most preferred.

Thyroparathyroidectomized (TPTX) Rat Model

The polyphosphonates are evaluated for in vivo bone resorption inhibition potency by an animal model system known as the thyroparathyroldectomized (TPTX) rat model. The general principles of this model system are disclosed in Russell et al., *Calcif. Tissue Research*, 6, 183–196 (1970), and in Muhlbauer and Fleisch, *Mineral Electrolyte Metab.*, 5, 296–303 (1981), the disclosures of which are incorporated herein by reference. The basic biochemical concept of the TPTX system is inhibition of the parathyroid hormone (PTH) - induced rise in serum and ionized calcium levels by the respective bone active polyphosphonates.

Materials and Methods

Materials

Low calcium and low phosphorous diets used were prepared by Teklad ® Test Diets (Harlan Industries, Madison, Wis. 53711; Order #TD82195) in a pellet form of approximately 0.18% calcium and 0.22% phosphorous. The diets contained all the essential vitamins and minerals required for the rat, with the exception of calcium and phosphorous. The calcium and phosphorous levels of the pellets were verified analytically (Procter & Gamble Co., Miami Valley Laboratories, Cincinnati, Ohio).

PTH was acquired as a powdered bovine extract (Sigma Chemical Co., P.O. Box 14508, St. Louis, Mo., order #P0892, Lot #72F-9650) at an activity of 138 USP units per mg. PTH was prepared in 0.9% saline such that the final concentration was 100 U.S.P./ml. All solutions were filtered through a #4 Whatman Filter Paper and refiltered through a 0.45 $\mu$m Metricel ® filter.

Dose Solutions and Dosing Procedure

All solutions of compounds to be tested for bone resorption inhibition potency were prepared for subcutaneous injection in 0.9% normal saline and adjusted to pH 7.4 using NaOH and/or HCl. Dose solution calculation was made by considering the mass of powder (based on molecular weight, hydration) of the active material in mg/kg (body weight) that corresponds to mg P/kg. Concentrations were based on dosing 0.2 ml/100 grams of body weight. Initially, all compounds were administered at 0.01, 0.1, 1.0, and sometimes 10 mg P/kg/day for 4 days. Where necessary the test was repeated, whereby the animals were administered with 0.5 X and 0.2 X LED in order to refine the determination of LED. Adjustments in dosage based on changes in body weight were made on a daily basis.

Animals

In this study 50 male Wistar rats weighing approximately 150–160 grams were thyroparathyroidectomized surgically by the breeder (Charles River Breeding Laboratories). All rats were double housed on arrival in suspended cages with Purina Laboratory Rodent Chow ® and tap water ad libitum. After acclimation to the laboratory environment for 3–5 days, the rats were placed on a low calcium, low phosphorous (0.18%/0.22%) diet (Teklad ®) and given 2% (W/V) calcium gluconate supplemented deionized water via water bottles.

Method

On day four of low-calcium diet all rats were anesthetized with Ketaset ® (Ketamine Hydrochloride, 100 mg/ml, Bristol Myers), 0.10 ml/100 grams of body weight, weighed and then bled from the retro-orbital venous plexus for serum total calcium analysis using Flame Atomic Absorption (FAA). All rats weighing less than 180 grams were eliminated from the study. Animals were then randomized statistically such that the mean total serum calcium for each group was the same. Only rats deemed hypocalcemic (total serum calcium $\leq 8.0$ mg/dl) were placed in study groups comprising six animals per group.

Treatments with the various compounds commenced on day 6 and lasted through day 9 of the study (at 1:00 P.M. each day). Dose solutions were prepared to be given at constant rate of 0.2 ml/100 grams of body weight subcutaneously in the ventral skin flap where the hind leg meets the torso. All rats were weighed and dosed daily. A 25 gauge ⅜" needle was used to administer drug, alternating dose sites daily. On day 8, animals were changed to deionized, distilled water via bottles. On day 9 all rats were fasted in the afternoon at approximately 4:00 P.M. On day 10 of study no treatment was given. In the morning a 600 μl sample of whole blood was collected from each rat in Microtainer (B-D#5060) serum separator tubes for serum total calcium (FAA). Two 125 μl samples of heparinized whole blood were also collected to be used for ionized calcium analysis. Immediately following blood collection all rates were weighed and injected with bovine parathyroid hormone subcutaneously at a rate of 75 USP (filtered) per 100 grams of body weight. Blood sampling for total and ionized calcium was repeated three and one-half hours post-PTH injection.

All pre- and post-PTH total and ionized calciums were statistically analyzed for significance compared to PTH alone (control) using Students t-test, analysis of variance, and their non-parametric equivalents. The post minus pre-change and % change were also determined on calcium levels and pre-drug vs post-drug body weights.

The physiological effect of the PTH challenge is a rise in serum calcium level, with peak activity observed at three and one-half hours. Since the hormonal and dietary controls of calcium metabolism are minimized in the TPTX model, an observed increase in serum calcium level is presumably the result of resorption of bone material. Since polyphosphonates tend to inhibit resorption of bone materials, the animals pretreated with polyphosphonate showed a rise in serum calcium level after PTH challenge which was less than that found in control animals which had been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. The LED values of the bone resorption inhibition potency of representative bone resorption inhibiting polyphosphonate compounds as determined by the TPTX rat model are presented in Table I.

TABLE I

| Diphosphonate Compound | Lowest Effective (Antiresorptive) Dose TPTX LED (mg P/kg) |
|---|---|
| EHDP | 1.0 |
| Cl₂MDP | 0.5 |
| APD | 0.1 |
| ABDP | 0.01 |
| AHDP | 0.1 |
| N—(2-pyr)AMDP | 0.01 |
| pyr-EDP | 0.01 |
| pyr-EHDP | 0.001 |
| HIP | 1.0 |

Schenk Model

The polyphosphonates are evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87–99 (1983); and in Schenk et al., *Calcif. Tissue Res.* 11, 196–214 (1973), the disclosures of which are incorporated herein by reference.

Materials and Methods

Animals

Preweaning 17-day-old (30 gms) male Sprague Dawley rats (Charles River Breeding Laboratories) were shipped with their mothers and placed in plastic cages with their mothers upon arrival. At 21 days of age, pups receiving Rat Chow and water ad libitum were randomly allocated into treatment groups comprising five animals per group, except for control animals receiving saline vehicle which had 10 rats per group. On day 0 and again on day 1 all animals were given a subcutaneous injection of Calcein (Sigma) as a 1% solution in 0.9% NaCl solution to label the skeleton.

Dose Solutions and Dosing Procedure

All solutions were prepared for subcutaneous injection in 0.9% normal saline and adjusted to pH 7.4 using NaOH and/or HCl. Dose solution calculation was made by considering the mass of powder (based on molecular weight, hydration) of the active material in mg/kg (body weight) that corresponds to mg P/kg. Concentrations were based on dosing 0.2 ml/100 g body weight. Initially, all compounds were administered at 0.1, 1.0 and 10.0 mg P/kg/day for 7 days. Compounds showing activity at 0.1 mg P/kg/day were then tested at logarithmic decrements down to 0.001 mg P/kg/day. Adjustments in dosage based on changes in body weight were made on a daily basis.

Necropsy, Tissue Processing and Histomorphometry

On day 8 after the start of dosing, all animals were sacrificed by CO₂ asphyxiation. Tibias were dissected free and placed in 70% ethyl alcohol. One tibia was dehydrated in graded ethanol solutions and embedded in methyl methacrylate using a rapid procedure described in Boyce et al., *Lab. Investig.*, 48, 683–689 (1983), the disclosures of which are incorporated herein by reference. The tibia was sectioned longitudinally through the metaphyseal area (Leitz ® saw microtome at 150μ). Specimens were stained on one surface with silver nitrate and mounted on microscope slides for evaluation with a Quantimet Image Analyzer (Cambridge Instruments, Inc.) using both incandescent and ultraviolet illumination. Metaphyseal trabecular bone content was measured in the region between the fluoresent label and the growth plate: expressed as percent of total area (bone+marrow). Epiphyseal growth plate width was obtained as the mean value of 10 equally-spaced measurements across the section.

Statistical evaluation of data was made using parametric and non-parametric analysis of variance and Wilcoxon's rank sum test to determine a statistically significant effect compared to control animals.

The Schenk model provided data for in vivo bone resorption inhibition by the compounds. The lowest effective (antiresorptive) dose ("LED") for representative compounds tested, as determined by the Schenk model, are provided in Table II.

TABLE II

| Diphosphonate Compound | Lowest Effective (Antiresorptive) Dose Schenk LED (mg P/kg) |
|---|---|
| EHDP | 1.0 |
| Cl₂MDP | 0.5 |
| APD | 0.1 |
| ABDP | 0.1 |
| AHDP | 0.1 |

TABLE II-continued

| Lowest Effective (Antiresorptive) Dose | |
|---|---|
| Diphosphonate Compound | Schenk LED (mg P/kg) |
| N—(2-pyr)AMDP | 0.01 |
| pyr-EDP | 0.01 |
| pyr-EHDP | 0.001 |
| HIP | 1.0 |

Diphosphonate compounds which have a bone mineralization inhibiting effect cause widening of the epiphyseal growth plate, since matrix production continues but mineralization is impeded. The widening of the epiphyseal growth plate as observed in the Schenk model is, therefore, a measure of the mineralization inhibiting effect of the diphosphonate compound tested.

The lowest tested dosages producing a statistically significant widening of epiphyseal growth plate for compounds tested are given in Table III.

TABLE III

| Mineralization Inhibition (Schenk Model) | |
|---|---|
| Diphosphonate Compound | Lowest tested dosage producing a statistically significant widening of epiphyseal growth plate (mg P/kg) |
| EHDP | 5 |
| APD | 10 |
| Cl$_2$MDP | — |
| ABDP | —[1] |
| AHDP | 10 |
| N—(2-pyr)AMDP | 0.1[2] |
| pyr-EDP | —[1] |
| pyr-EHDP | —[2] |
| HIP | — |

— = No plate widening observed at highest dose tested (highest dose tested is 10 mg P/kg/day unless otherwise indicated)
1 = Highest dose evaluated is 1 mg P/kg/day (compound lethally toxic at 10 mg P/kg/day)
2 = Highest dose evaluated is 0.1 mg P/kg/day (compound lethally toxic at 1 mg P/kg/day).

The present invention further relates to a kit for conveniently and effectively implementing the method of treatment utilizing the cyclic regimen of the present invention. This kit would be suited for use in a cyclic regimen for the treatment or prevention of osteoporosis, in humans or lower animals afflicted with or at risk to osteoporosis, said cyclic regimen comprising alternating for two or more cycles the administration of a bone resorption inhibiting polyphosphonate and a rest period, said kit containing the following components:

(a) from about 1 to about 90 daily doses, each dose containing a limited and effective amount of a bone resorption inhibiting polyphosphonate, with from about 0.25×LED to about 4×LED of polyphosphonate preferred, and from about 0.25×LED to about 2.5×LED of polyphosphonate most preferred; and (b) from about 50 to about 120 daily doses, preferred being from about 70 to about 100 daily doses, with about 84 daily doses most preferred, of a placebo or a nutrient supplement; and a means for having the components arranged in a way as to facilitate compliance with the regimen. Preferred periods for administering the polyphosphonates, preferred dosages, preferred cycle times, preferred rest periods, preferred polyphosphonates, and other preferred values for use in a kit of the present invention are as described more fully above for the method of treatment of the present invention.

Assuming that the majority of subjects afflicted with or at risk to osteoporosis weigh between about 10 kg and 100 kg, the range of the daily safe and effective amount of the preferred bone resorption inhibiting polyphosphonates for use in a kit of the present invention are: EHDP: from about 2.5 mg P to about 400 mg P, with from about 2.5 mg P to about 250 mg P preferred; Cl$_2$MDP: from about 1.2 mg P to about 500 mg P, with from about 1.2 mg P to about 200 mg P preferred, and with from about 1.2 mg P to about 125 mg P most preferred; APD: from about 0.25 mg P to about 100 mg P, with from about 0.25 mg P to about 40 mg P preferred, and from about 0.25 mg P to about 25 mg P most preferred; ABDP from about 0.025 mg P to about 10 mg P, with from about 0.025 mg P to about 4 mg P preferred, and from about 0.025 mg P to about 2.5 mg P most preferred; AHDP: from about 0.25 mg P to about 100 mg P, with from about 0.25 mg P to about 40 mg P preferred, and from about 0.25 mg P to about 25 mg P most preferred; pyr-EDP: from about 0.025 mg P to about 10 mg P, with from about 0.025 mg P to about 2.5 mg P most preferred; with from about 0.025 mg P to about 2.5 mg P most preferred; pyr-EHDP: from about 0.0025 mg P to about 1.0 mg P, with from about 0.0025 mg P to about 0.4 mg P preferred, and from about 0.0025 mg P to about 0.25 mg P most preferred; HIP: from about 2.5 mg P to about 1000 mg P, with from about 2.5 mg P to about 400 mg P preferred, and from about 2.5 mg P to about 250 mg P most preferred.

Strict compliance with the above-described cyclic regimen is believed to be essential for its success. The kit of the present invention is designed to facilitate such strict compliance in that it provides a convenient and effective means for assuring that the patient takes the appropriate medication in the correct dosage on each day of the regimen.

In one specific embodiment of the invention said means is a card having arranged thereupon the components of the treatment regimen in the order of their intended use. An example of such a card is a so-called blister pack. Blister packs are well-known in the packaging industry, and are being widely used for the packaging of pharmaceutical unit dosage forms (tablets, capsules, and the like). Blister packs generally comprise a sheet of relatively stiff material, covered with a foil of a, preferably transparent, plastic material. During the packaging process, recesses are formed in the plastic foil. The recesses have the size and shape of the tablets or capsules to be packed. Next, the tablets or capsules are placed in the recesses, and the sheet of relatively stiff material is sealed against the plastic foil at the face of the foil which is opposite from the direction in which the recesses are formed. As a result, the tablets or capsules are sealed in the recesses, between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It is desirable to provide a memory aid on the card, e.g. in the form of numbers next to the tablets or capsules, whereby the numbers correspond with the days of the regimen which the tablets or capsules so specified should be ingested. Another example of such a memory aid is a calendar printed on the card, e.g. as follows "First Week, Monday, Tuesday, . . . , etc. . . . Second Week, Monday, Tuesday, . . . ", etc. Other variations of memory aids will be readily apparent. A "daily dose"

can be a single tablet or capsule or several pills or capsules to be taken on a given day. The memory aid should reflect this.

The term "card", as used herein, is not limited to a flat, sheet-like structure. The term includes structures as described above which are folded so as to reduce their planar dimensions; the term further includes a plurality of cards which, combined, contain the components for the treatment regimen. An example of the latter would be a stack of cards, marked "Week 1", "Week 2", etc., each containing the components of the regimen for one week of treatment. The tablets or capsules may also be arranged on a narrow strip, one after the other; the material of the strip is preferably flexible, so that it can be wound on a reel. The strip may be perforated so that daily doses can be torn off.

In another specific embodiment of the invention said means is a dispenser designed to dispense said daily doses, one at a time, in the order of their intended use. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered micro-chip memory coupled with a liquid crystal readout, or audible reminder signal which, for example, reads out the data that the last daily dose has been taken and/or reminds one when the next dose is to be taken.

Single-unit dispensers are well-known and are being widely used in, e.g., vending machines. The concepts of such machines are directly suitable for, or easily adaptable to, use in the dispensers of this embodiment of the present invention.

Specific examples of the method of treatment of the present invention, and of kits for assuring the necessary strict compliance with the regimen according to the method of treatment of the present invention, are:

EXAMPLE I

Patients clinically diagnosed as suffering from osteoporosis are subjected to a treatment regimen according to the present invention as follows.

Each patient is subjected to from 3 to 8 cycles, each cycle consisting of (a) a period of 14 days during which the patients receive 5 mg/kg/day of DIDRONEL (Norwich Eaton Pharmaceuticals, Norwich, N.Y.); and (b) a rest period of 84 days during which the patients receive a diet which is verified to contain a minimum of 1 g/day of calcium.

The treatment regimen results in a significant alleviation of osteoporotic conditions. The use of the above regimen by patients at risk to osteoporosis, for example postmenopausal women, has a prophylactic effect against the onset of osteoporosis in the patients.

A kit for use in a regimen for treatment or prevention of osteoporosis, as described above, is made up as follows:

Three slip cases, each case being 4¾ in. wide×8½ in. high×6 in. deep (about 12 cm×21½ cm×15 cm) and containing 13 cards (blister packs) of 4¾ in.×8½ in. (about 12 cm×21½ cm), are boxed side by side in a box 8½ in. wide×6 in. high×14¼ in. deep (about 21½ cm×15 cm×36 cm). The box opens on the 8½ in.×6 in. side (about 21½ cm×15 cm) to allow the first slip case, which contains the first cycle's doses, to be removed. The second and third slip cases cannot be removed from the box until the preceding case has been removed. The first card in this slip case contains 14 tablets, each tablet containing 400 mg DIDRONEL (Norwich Eaton Pharmaceuticals, Norwich, N.Y.). The tablets are arranged in 4 rows of 3 tablets per row, and a 5th row with 2 tablets in the row. Printed on the card, next to each tablet, are the words "Day 1", "Day 2", ... etc. through "Day 14".

The remaining 12 cards each contain 14 capsules, each capsule containing 500 mg of calcium. Printed on each card are rectangular boxes, such that each box contains two capsules (i.e., 7 boxes per card; one daily dose is two capsules, each capsule containing 500 mg of calcium for a total daily dose of 1 g of calcium). The boxes are marked "Day 15", "Day 16", ... etc. through "Day 98" on the last card.

After all the doses which are contained in the first slip case have been taken (i.e., after day 98), the second slip case (i.e., cycle two of the treatment regimen) is removed from the box. This slip case contains 13 cards containing tablets arranged as in the first slip case, except the days noted on the cards correspond to the day of the treatment for the second cycle. Thus, the DIDRONEL tablets are marked as "Day 99" through "Day 112", and the calcium tablets to be taken during the rest period are marked as "Day 113" through "Day 196". The third slip case, which is removed last from the box after day 196, is similarly organized for days 197 through 294. The last card of this third slip case may contain a printed reminder that a renewal prescription should be obtained.

EXAMPLE II

Patients clinically diagnosed as suffering from osteoporosis are subjected to a treatment regimen according to the present invention as follows. Each patient is subjected to from 3 to 8 cycles, each cycle consisting of (a) a period of 84 days during which the patients receive 20 mg/kg/day of disodium $Cl_2MDP$ and (b) a rest period of 84 days during which the patients receive a diet which is verified to contain a minimum of 1 g/day of calcium.

The treatment regimen results in a significant alleviation of osteoporotic conditions. The use of the above regimen by patients at risk to osteoporosis, for example postmenopausal women, has a prophylactic effect against the onset of osteoporosis in the patients.

A kit for use in a regimen for treatment or prevention of osteoporosis, as described above, is made as indicated in Example I, with this kit having tablets totalling 1400 mg/day of disodium $Cl_2MDP$ and the number of cards increased and labeled to accommodate 84 days of dosing with disodium $Cl_2MDP$ per slip case (i.e., per cycle).

The treatment regimen is varied, for example, as indicated in Table IV.

TABLE IV

| | Polyphosphonate dosing | | | | |
|---|---|---|---|---|---|
| Compound | Period (days) | Dose/day (mg P/kg) | Rest Period (days) | Total Cycle (days) | Number of Cycles |
| $Cl_2MDP$ | 28 | 2.5 | 84 | 112 | 7 |
| EHDP | 28 | 2.5 | 84 | 112 | 5 |
| APD | 14 | 0.5 | 70 | 84 | 4 |
| AHDP | 60 | 0.03 | 50 | 110 | 3 |
| ABDP | 21 | 0.005 | 110 | 131 | 5 |
| N—(2-pyr)EDP | 70 | 0.01 | 100 | 170 | 5 |
| N—(2-pyr)EHDP | 10 | 0.0005 | 120 | 130 | 8 |

TABLE IV-continued

| | Polyphosphonate dosing | | | | |
|---|---|---|---|---|---|
| Compound | Period (days) | Dose/day (mg P/kg) | Rest Period (days) | Total Cycle (days) | Number of Cycles |
| HIP | 50 | 1 | 90 | 140 | 7 |

A treatment regimen consisting of the above cycles results in an appreciable alleviation of osteoporotic conditions in patients clinically diagnosed as suffering from osteoporosis. Also, in patients at risk to osteoporosis, a treatment regimen consisting of the above cycles has a prophylactic effect against the onset of osteoporosis in these patients.

EXAMPLE III

Postmenopausal osteoporotic females with spinal compression fractures are subjected to a treatment regimen according to the present invention as follows.

Each patient is subjected to three cycles which utilize about 20 mg/kg/day of disodium $Cl_2MDP$ according to the following regimen: 28 days of daily dosing with disodium $Cl_2MDP$, followed by an 84 day rest period, followed by 84 days of daily dosing with disodium $Cl_2MDP$, followed by an 84 day rest period, followed by 28 days of daily dosing with disodium $Cl_2MDP$. This regimen results in a substantial increase in total bone mass in patients receiving treatment according to the regimen of the present invention.

What is claimed is:

1. A method for treating osteoporosis, in humans or lower animals afflicted with or at risk to osteoporosis, comprising administering to said human or lower animal an effective amount of a bone resorption inhibiting polyphosphonate according to the following schedule:
   (a) a period of from about 1 day to about 90 days during which said bone resorption inhibiting polyphosphonate is administered daily in a limited amount; followed by
   (b) a rest period of from about 50 days to about 120 days; and
   (c) repeating (a) and (b) two or more times where a net increase in bone mass said human or animal results.

2. A method according to claim 1 wherein the bone resorption inhibiting polyphosphonate is administered daily in an amount of from about 0.25×LED to about 4×LED.

3. A method according to claim 2 wherein the bone resorption inhibiting polyphosphonate is administered daily in an amount of from about 0.25×LED to about 2.5×LED.

4. A method according to claim 1 wherein the bone resorption inhibiting polyphosphonate has a dose at which mineralization inhibition is observed which is greater than about 10 times the LED for bone resorption inhibition, and is administered daily in an amount of from about 0.25×LED to about 10×LED.

5. A method according to claim 4 wherein the bone resorption inhibiting polyphosphonate is administered daily in an amount of from about 0.25×LED to about 4×LED.

6. A method according to claim 5 wherein the bone resorption inhibiting polyphosphonate is administered daily in an amount of from about 0.25×LED to about 2.5×LED.

7. A method according to claim 4 wherein the rest period is from about 70 days to about 100 days.

8. A method according to claim 7 wherein the bone resorption inhibiting polyphosphonate is administered daily over a period of about 84 days, and the rest period is from about 70 days to about 100 days.

9. A method according to claim 1 wherein the bone resorption inhibiting polyphosphonate has a dose at which mineralization inhibition is observed which is less than or equal to about 10× the LED for bone resorption inhibition, and is administered daily in an amount of from about 0.25×LED to about 4×LED.

10. A method according to claim 9 wherein the bone resorption inhibiting polyphosphonate is administered daily in an amount of from about 0.25×LED to about 2.5×LED.

11. A method according to claim 9 wherein the bone resorption inhibiting polyphosphonate is administered daily over a period of from about 1 day to about 30 days.

12. A method according to claim 10 wherein the bone resorption inhibiting polyphosphonate is administered daily over a period of from about 1 day to about 30 days.

13. A method according to claim 12 wherein the rest period is from about 70 days to about 100 days.

14. A method according to claim 13 wherein the bone resorption inhibiting polyphosphonate is administered daily over a period of about 14 days, and the rest period is from about 70 days to about 100 days.

15. A method according to claim 1 wherein the bone resorption inhibiting polyphosphonates, and daily dosage ranges, are selected from the group consisting of:
Ethane-1-hydroxy-1,1-diphosphonic acid: from about 0.25 mg P/kg to about 4 mg P/kg;
Dichloromethane diphosphonic acid: from about 0.12 mg P/kg to about 5 mg P/kg;
Propane-3-amino-1-hydroxy-1,1-diphosphonic acid: from about 0.025 mg P/kg to about 1 mg P/kg;
Butane-4-amino-1-hydroxy-1,1-diphosphonic acid: from about 0.0025 mg P/kg to about 0.1 mg P/kg;
Hexane-6-amino-1-hydroxy-1,1-diphosphonic acid: from about 0.025 mg P/kg to about 1 mg P/kg;
2-(2-pyridyl-ethane-1,1-diphosphonic acid: from about 0.0025 mg P/kg to about 0.1 mg P/kg;
2-(2-pyridyl)-1-hydroxy-ethane-1,1-diphosphonic acid: from about 0.00025 mg P/kg to about 0.01 mg P/kg; and/or
Hexahydroindan-2,2-diphosphonic acid: from about 0.25 mg P/kg to about 10 mg P/kg;
and their pharmaceutically-acceptable salts and esters.

16. A method according to claim 15 wherein the bone resorption inhibiting polyphosphonates, and daily dosage ranges, are selected from the group consisting of:
Ethane-1-hydroxy-1,1-diphosphonic acid: from about 0.25 mg P/kg to about 2.5 mg P/kg;
Dichloromethane diphosphonic acid: from about 0.12 mg P/kg to about 1.25 mg P/kg;
Propane-3-amino-1-hydroxy-1,1-diphosphonic acid: from about 0.025 mg P/kg to about 0.25 mg P/kg;
Butane-4-amino-1-hydroxy-1,1-diphosphonic acid: from about 0.0025 mg P/kg to about 0.025 mg P/kg;
Hexane-6-amino-1-hydroxy-1,1-diphosphonic acid: from about 0.025 mg P/kg to about 0.25 mg P/kg;
2-(2-pyridyl-ethane-1,1-diphosphonic acid: from about 0.0025 mg P/kg to about 0.025 mg P/kg;

2-(2-pyridyl)-1-hydroxy-ethane-1,1-diphosphonic acid: from about 0.00025 mg P/kg to about 0.0025 mg P/kg; and/or Hexahydroindan-2,2-diphosphonic acid: from about 0.25 mg P/kg to about 2.5 mg P/kg;

and their pharmaceutically-acceptable salts and esters.

17. A method according to claim 13 wherein the bone resorption inhibiting polyphosphonate is ethane-1-hydroxy-1,1-diphosphonic acid, or its pharmaceutically-acceptable salts or esters.

18. A method according to claim 4 wherein the bone resorption inhibiting polyphosphonate is hexane-6-amino-1-hydroxy-1,1-diphosphonic acid, or its pharmaceutically-acceptable salts or esters.

19. A method according to claim 4 wherein the bone resorption inhibiting polyphosphonate is dichloromethane diphosphonic acid, or its pharmaceutically-acceptable salts or esters.

20. A method according to claim 19 wherein each cycle comprises: (a) a period of about 84 days during which $Cl_2MDP$, or its pharmaceutically-acceptable salts or esters, is administered daily in an amount of about 4 mg P/kg; followed by (b) a rest period of about 84 days.

21. A method according to claim 17 wherein each cycle comprises: (a) a period of about 14 days during which EHDP, or its pharmaceutically-acceptable salts or esters, is administered daily in an amount of about 1.25 mg P/kg; followed by (b) a rest period of about 84 days.

* * * * *